(12) United States Patent
Kamimoto et al.

(10) Patent No.: US 6,371,920 B1
(45) Date of Patent: Apr. 16, 2002

(54) PULSE WAVE DETECTING DEVICE

(75) Inventors: Takashi Kamimoto; Masataka Shinogi; Hiroshi Odagiri; Kazumi Sakumoto; Keisuke Tsubata; Chiaki Nakamura, all of Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/552,439

(22) Filed: Apr. 18, 2000

(30) Foreign Application Priority Data

Apr. 21, 1999 (JP) .......................................... 11-113294

(51) Int. Cl.⁷ ................................................ A61B 5/02
(52) U.S. Cl. ........................ 600/481; 600/500; 600/503; 600/438
(58) Field of Search .............................. 600/481, 485, 600/500–503, 372, 382, 384, 393, 438

(56) References Cited

U.S. PATENT DOCUMENTS

| | | | | |
|---|---|---|---|---|
| 4,841,780 A | * | 6/1989 | Inada et al. ............... | 73/861.06 |
| 5,307,816 A | * | 5/1994 | Hashimoto et al. ..... | 600/439 X |
| 5,523,058 A | * | 6/1996 | Umemura et al. ...... | 422/128 X |
| 6,176,832 B1 | * | 8/1998 | Habu et al. ............. | 600/485 X |

\* cited by examiner

Primary Examiner—John P. Lacyk
Assistant Examiner—Ryan Carter
(74) Attorney, Agent, or Firm—Adams & Wilks (57) ABSTRACT

A pulse wave monitor having a structure capable of automatically performing optimal positioning of a pulse wave probe with respect to a user's body. A plurality of transmitting piezoelectric vibrators for transmitting an ultrasonic wave to an artery are provided along with a plurality of receiving piezoelectric vibrators for receiving an ultrasonic wave from the artery. An optimal combination of a transmitting piezoelectric vibrator and a receiving piezoelectric vibrator for use in pulse wave measurement is determined based on the intensity of a received ultrasonic wave signal. Ultrasonic wave transmission and reception are made by the optimal combination so that accurate pulse wave detection measurement is made possible by automatic positioning of the pulse wave probe.

18 Claims, 5 Drawing Sheets

PRIOR ART

FIG. 5B

PRIOR ART

PULSE WAVE DETECTING DEVICE

BACKGROUND OF THE INVENTION

The present invention relates to pulse wave detecting devices and, more particularly, to a pulse wave detecting device for detecting a pulse wave by transmitting and receiving an ultrasonic wave to and from an artery.

It is broadly implemented to detect a pulse wave from blood flow through an artery, at medical sites or in health care. Pulse wave detection is broadly conducted by electronically, automatically detecting a pulse frequency or the like by using a pulse wave detecting device, besides detecting of a pulse frequency per a given time through palpation.

The devices which electronically detect a pulse wave and acquire a pulse frequency include those having a piezo-type piezoelectric element that is to be positioned as a sensor over an artery in order to detect a pulse frequency from a pressure change of a surface skin caused due to an artery pressure change (surface skin displacement by pressure) and those using an ultrasonic wave to detect a pulse frequency.

The pulse wave detecting devices using an ultrasonic wave include those utilizing the Doppler effect due to blood flow, as proposed, e.g. in Japanese Patent Laid-open No. 214335/1989 and U.S. Pat. No. 4,086,916.

Figure 5A:
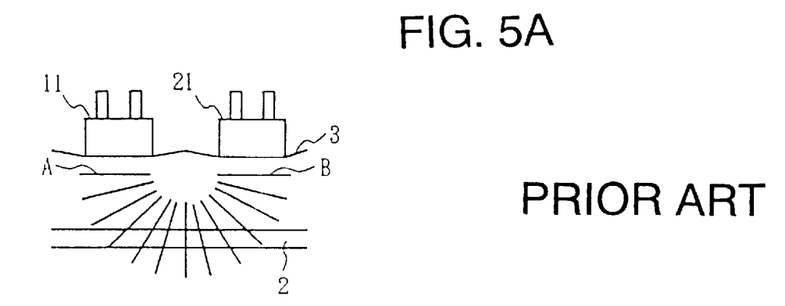
FIGS. 5A and 5B are view for explaining a conventional pulse wave detecting device.
Figure 5B:
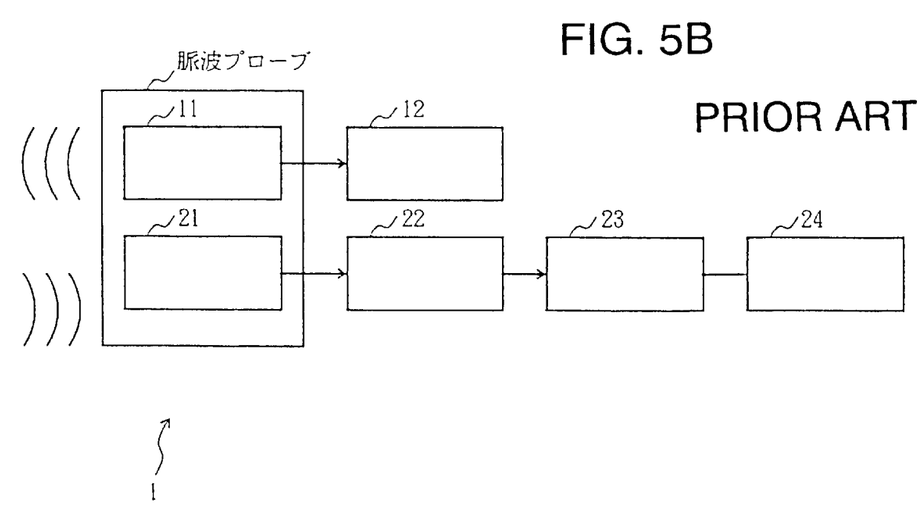

With reference to FIGS. 5A and 5B, the conventional pulse wave detecting device 1 will be explained on its basic structure and operation.

The pulse wave detecting device 1 is mounted on a wrist watch and used as below.

First, a pulse wave probe having an ultrasonic wave transmitting transducer 11 and ultrasonic wave receiving transducer 21 formed by a plurality of piezoelectric vibrators is slidably mounted by screwing in an optimal position of a watch strap for detecting a pulse wave (e.g. in a position where the pulse wave detection signal assumes a maximum).

When actually detecting a pulse wave by the pulse wave detecting device 1, as shown in FIGS. 5A and 5B an ultrasonic wave A is transmitted from the piezoelectric element of the ultrasonic wave transmitting transducer 11 driven by a drive part 12 toward an artery 2 in a human body surface 3. Then, a reflection wave B reflected by the blood flowing through the artery 2 is received by the ultrasonic wave receiving transducer 21.

Next, the reflection ultrasonic wave B thus received is waveform-detected by a receiving part 22. The waveform-detected ultrasonic wave is processed in a signal processing part 23 to detect a change in frequency or phase of the reflection wave B. The signal processed by the signal processing part 23 is displayed of its waveform on a display device of an output part 24.

When the heart contracts, the blood flowing through the artery 2 is high in speed. Accordingly, the reflection wave of ultrasonic wave transmitted toward the artery 2 is increased in frequency due to the Doppler effect. Conversely, when the heart expands the blood flowing speed is low and hence the frequency thereof decreases.

In this manner, an ultrasonic wave is radiated to a blood flow in an artery varying in speed depending on heart pulsation. By detecting a change of frequency, it is possible to detect a pulse wave, and furthermore a pulse frequency or a blood flow speed.

However, the above pulse wave detecting device 1 has the following defects.

First, when wearing the wrist watch type pulse wave detecting device 1 on a wrist, it takes time in adjusting and positioning, by sliding, the pulse wave probe to an optimal position for detecting a pulse wave.

Second, even where the wrist watch type pulse wave detecting device 1 be worn at an optimal position on the wrist, if the pulse wave probe is deviated in position because of a subsequent movement of the body or the like, then correct measurement would be impossible to conduct.

SUMMARY OF THE INVENTION

It is therefore a first object of the present invention to provide a pulse wave detecting device which is capable of automatically positioning a pulse wave probe in an optimal position when putting the pulse wave detecting device.

It is a second object of the invention to provide a pulse wave detecting device in which a pulse wave probe can be newly positioned automatically in an optimal position even when there is positional deviation in the pulse wave probe after wearing the pulse wave detecting device.

In the present invention, the first and second objects are achieved by a pulse wave detecting device comprising transmitting means having a plurality of transmitting piezoelectric vibrators to transmit an ultrasonic wave toward an artery, receiving means having a plurality of receiving piezoelectric vibrators to receive an ultrasonic wave propagating through the artery, pulse wave information acquiring means for acquiring pulse wave information from an ultrasonic wave signal transmitted from any one of the transmitting piezoelectric vibrators and received by any one of the receiving piezoelectric vibrators, signal intensity detecting means for detecting a signal intensity of the received ultrasonic wave by the receiving means, and optimal combination determining means for determining an optimal combination of a transmitting piezoelectric vibrator to be used by the transmitting means and a receiving piezoelectric vibrator to be used by the receiving means on the basis of the signal intensity of the ultrasonic wave detected by the signal intensity detecting means, and causing the transmitting piezoelectric vibrator of the optimal combination to transmit an ultrasonic wave and the receiving piezoelectric vibrator of the optimal combination to receive the ultrasonic wave.

Also, the optimal combination determining means has switching means to switch to any one of the transmitting piezoelectric vibrators and selecting means to select any one of the receiving piezoelectric vibrators, the optimal combination determining means causing the switching means and the selecting means to change in order over the transmitting piezoelectric vibrators and the receiving piezoelectric vibrators, respectively, and determining an optimal combination of the transmitting piezoelectric vibrator and the receiving piezoelectric vibrator assuming a maximum value in signal intensity of an ultrasonic wave.

Also, the optimal combination determining means causes the switching means and the selecting means to periodically change in order over the transmitting piezoelectric vibrators and the receiving piezoelectric vibrators, respectively, and determines an optimal combination of the transmitting piezoelectric vibrator and the receiving piezoelectric vibrator assuming a maximum value in signal intensity of an ultrasonic wave.

Also, the optimal combination determining means, when a signal intensity of an ultrasonic wave detected by the signal intensity detecting means decreases, causes the switching means and the selecting means to change in order over the transmitting piezoelectric vibrators and the receiving piezoelectric vibrators, respectively, and determines an optimal combination of the transmitting piezoelectric vibrator and the receiving piezoelectric vibrator assuming a maximum value in signal intensity of a ultrasonic wave.

DETAILED DESCRIPTION OF THE PREFERRED EMBODIMENT

Preferred embodiments of a pulse wave detecting device of the present invention will now be described with reference to FIG. 1 to FIG. 4.

(1) Outline of Embodiments (i) Scan measurement:

By a signal intensity measuring part 123 of a pulse wave detecting device 1000, any of transmitting piezoelectric vibrators 101A–101D is switched to through a switching part 111 and any of receiving piezoelectric vibrators 102A–102D is selected through a selecting part 121.

This process provides a total of 16 pairs of transmitting piezoelectric vibrator and receiving piezoelectric vibrator. While scanning for all the 16 pairs of transmitting piezoelectric vibrator 101A–101D and receiving piezoelectric vibrator 102A–102D, an ultrasonic wave is transmitted toward an artery through any of the transmitting piezoelectric vibrators 101A–101D and an ultrasonic wave propagating through the artery is received by any of the receiving piezoelectric vibrators 102A–102D.

After waveform-detecting the received ultrasonic wave signal by a receiving part 122, the ultrasonic wave signal thus waveform-detected is supplied to the signal intensity measuring part 123 where it is measured of a signal intensity. The signal intensity measuring part 123 determines, among signal intensities of the totally 16 pairs of transmitting piezoelectric vibrator 101A–101D and receiving piezoelectric vibrator 102A–102D, a pair representing a maximum intensity as an optimal pair for pulse wave detection.

(ii) Pulse wave detection measurement:

In order to enable transmitting/receiving an ultrasonic wave by the determined optimal pair, the signal intensity measuring part 123 supplies a switch instruction signal to the switching part 111 and a select instruction signal to the selecting part 121. The pulse detecting device 1000 causes the receiving part 122 to waveform-detect the ultrasonic wave obtained by the optimal pair and then a signal processing part 124 to acquire out of the waveform-detected ultrasonic wave signal a pulse wave signal and pulse frequency to be displayed on a display part of an output part 125.

(2) Detailed Embodiments

Figure 1:
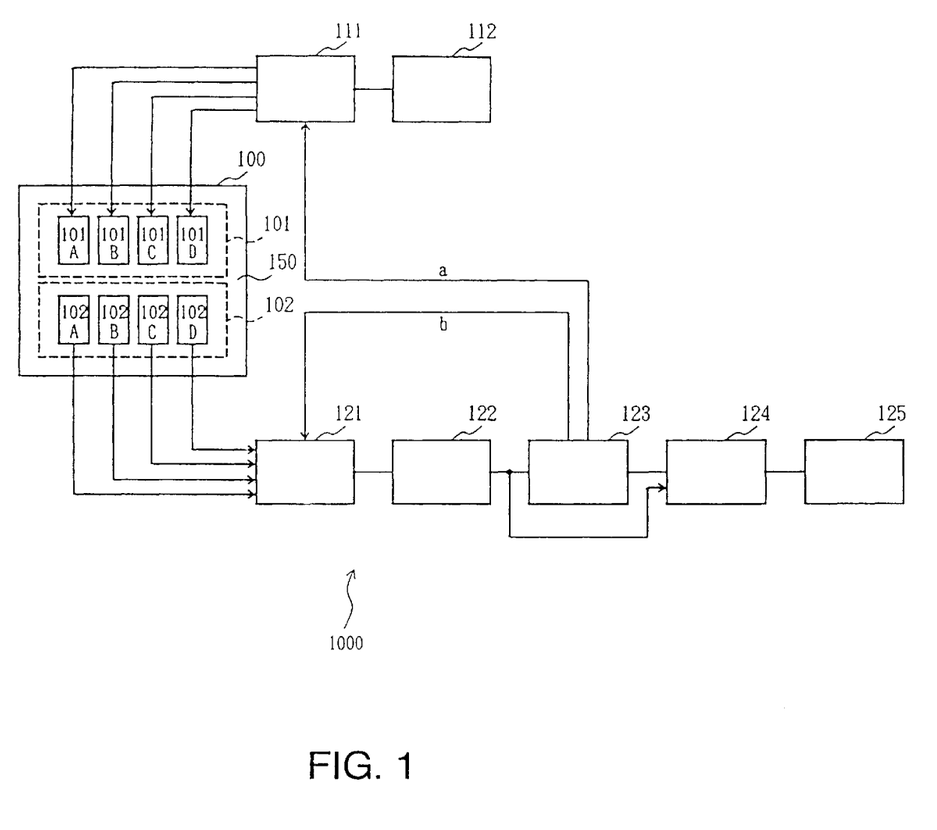
FIG. 1 is a block diagram showing a basic structure of a pulse wave detecting device.

FIG. 1 shows a block diagram illustrating a basic configuration of a pulse wave detecting device 1000 according to a preferred embodiment.

Figure 2A:
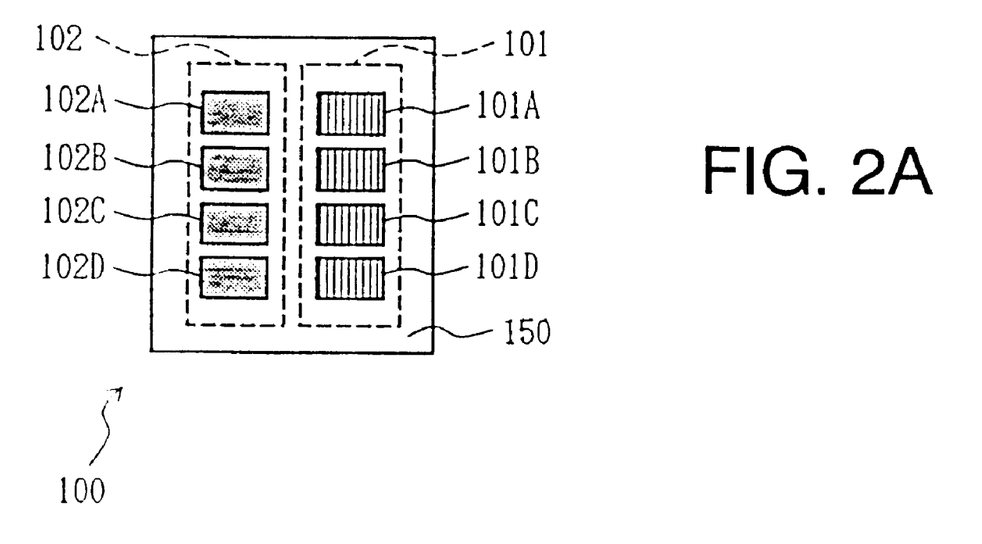
FIGS. 2A and 2B are view for explaining an arrangement of piezoelectric vibrators on a pulse wave probe provided in the pulse wave detecting device.
Figure 2B:
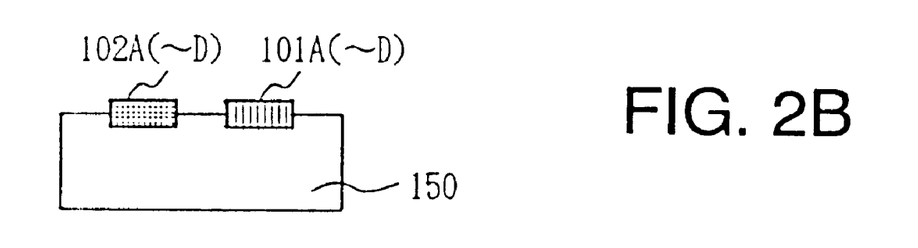

Referring first to FIG. 1 and FIG. 2, various constituent components will be explained of the pulse wave detecting device 1000.

As shown in FIG. 1, the pulse wave detecting device 1000 includes a pulse wave probe 100 having a transmitting transducer 101 and a receiving transducer 102, a switching part 111, a driving part 112, a selecting part 121, a receiving part 122, a signal intensity measuring part 123, a signal processing part 124 and an output part 125.

The transmitting transducer 101 and receiving transducer 102 are arranged on a pulse wave probe substrate 150 with 10 mm in length by 15 mm in width, and are further provided with the following constituent components.

The transmitting transducer 101 has four transmitting piezoelectric vibrators 101A, 101B, 101C and 101D (hereinafter referred to as "transmitting piezoelectric vibrators 101A–101D") each having a size, of 3 mm in length by 2 mm in width by 200 $\mu$m in thickness. The transmitting transducer 101 causes any piezoelectric vibrator switched by the switching part 111 to transmit an amplitude-modulated 32-kHz ultrasonic wave toward an artery. By thus rendering 32 kHz the transmitting frequency from the transmitting transducer 101, where arranging a pulse wave detecting device 1000 in a timepiece, that frequency is common to a transmitting frequency of the timepiece. Accordingly, a not-shown transmitter of the timepiece is commonly used in a driving circuit of the driving part 112. Outputting is made after amplification as required. This can reduce the number of parts needed for the pulse wave detecting device 1000, thus reducing manufacture cost.

The receiving transducer 102 has four receiving piezoelectric vibrators 102A, 102B, 102C and 102D (hereinafter referred to as "receiving piezoelectric vibrators 102A–102D") each having a size of 3 mm in length by 2 mm in width by 200 $\mu$m in thickness. The receiving transducer 102 causes any one of the receiving piezoelectric vibrators 102A–102D selected by the selecting part 121 to receive an ultrasonic wave transmitted from any one of the transmitting piezoelectric vibrators 101A–101D of the transmitting transducer 101 and propagating through a human body including an artery and to supply it to the receiving part 122.

The pulse wave probe 100 is a unit to function as a pulse wave sensor, which has the transmitting transducer 101 and receiving transducer 102 arranged on the common pulse probe substrate 150.

On the pulse wave probe 100, the transmitting piezoelectric vibrators 101A–101D (or the receiving piezoelectric vibrators 102A–102D) in a row of the pulse wave probe 100 shown in FIG. 1 are set up such that, when conducting pulse wave detection measurement, they are perpendicular to a radial artery, i.e. the transmitting transducer 101 and receiving transducer 102 are put in parallel in a direction of a radial artery blood flow and the transmitting piezoelectric vibrators 101A–101D and receiving piezoelectric vibrators 102A–102D are in contact with a body surface.

The arrangement of the receiving piezoelectric vibrators 102A–102D and the transmitting piezoelectric vibrators 101A–101D is further explained with reference to FIGS. 2.

FIG. 2A is a top view of the pulse wave probe 100. As shown in FIG. 2A, the four transmitting piezoelectric vibrators 101A–101D are arranged at equal intervals in a row form in a lengthwise direction (vertical direction) of the pulse wave probe substrate 150. The four receiving piezoelectric vibrators 102A–102D are arranged at equal intervals in a row form in parallel with and with a spacing by a constant distance from the lengthwise row of the transmitting piezoelectric vibrators 101A–101D. Furthermore, each pair of the transmitting and receiving piezoelectric vibrators 101A and 102A, 101B and 102B, 101C and 102C and 101D and 102D is arranged in a perpendicular direction to the lengthwise direction (horizontal direction) of the pulse wave probe substrate 150.

FIG. 2B is a sectional view of FIG. 2A wherein the transmitting piezoelectric vibrators 101A–101D and the receiving piezoelectric vibrators 102A–102D are arranged on the substrate 150. As shown in FIG. 2B, the transmitting piezoelectric vibrators 101A–101D and receiving piezoelectric vibrators 102A–102D are fitted in respective depressions formed in the pulse wave probe substrate 150, and fixed such that the piezoelectric vibrators at top surfaces are substantially in flush with each other.

The switching part 111 (FIG. 1) receives a switch instruction signal supplied from the signal intensity measuring part 123 through a signal line a, and switches so that an ultrasonic wave can be transmitted from any of the transmitting piezoelectric vibrators 101A–101D.

The driving part 112 has a transmitting source of an oscillator such as of quartz to generate an alternating current at a frequency dependent upon its eigenfrequency, and frequency-divide the same frequency into a 32-kHz high frequency. The driving part 112 drives by the 32-kHz high frequency any of the transmitting piezoelectric vibrators 101A–101D switched by the switching part 111, thus transmitting an ultrasonic wave.

Incidentally, the driving part 112 is driven by turning on a power to the pulse wave detecting device 1000. The selecting part 121 receives a select instruction signal supplied through a signal line b and selects any of the receiving piezoelectric vibrators 102A–102D.

The receiving part 122 waveform-detects the ultrasonic wave received by any of the receiving piezoelectric vibrators 102A–102D and supplies a waveform-detected ultrasonic wave to the signal intensity measuring part 123 and signal processing part 124.

The signal intensity measuring part 123 measures a signal intensity of the ultrasonic wave having been waveform-detected by the receiving part 122 after received by any one of the receiving piezoelectric vibrators 102A–102D, with respect to the ultrasonic wave transmitted from any one of the transmitting piezoelectric vibrators 101A–101D.

The signal processing part 124 has a not-shown pulse wave information acquiring part and pulsation count part. This pulsation information acquiring part has a not-shown count part to count a pulse frequency based on a signal supplied from the receiving part 122. This count part measures a time interval of pulse waves by a predetermined number of times (e.g. three times, five times, seven times, ten times, etc.), and determines a pulse frequency per minutes from a mean time T of rounds of measurements according to the following Equation (1).

$$V=60/T \quad (1)$$

Incidentally, there is no limitation to the case where determining a pulse frequency from a mean time T of pulse waves. For example, a pulse count w in a predetermined time t (e.g. 10 seconds) may be detected and a pulse frequency V per minute may be determined according to the following Equation (2).

$$V=w\times(60/t) \quad (2)$$

In the count part, a pulse wave signal is generated that represents a presence of a pulse wave such as a pulse signal on each pulse wave, which is to be supplied together with a determined pulse frequency to the output part 125.

The output part 125 has a not-shown display part to display a pulse frequency and pulse wave signal supplied from the pulsation count part of the signal processing part 124. The display part is structured by a liquid crystal display to image-display a pulse frequency and pulse wave signal. Alternatively, a pulse frequency may be electrically displayed on a panel.

The overall operation of the pulse wave detecting device 1000 will now be explained by separating as (i) scan measurement and (ii) pulse wave detection measurement, with reference to FIG. 1.

(i) Scan measurement

By scan measurement explained below, an optimal pair is determined for pulse wave detection which is a combination of any one of the transmitting piezoelectric vibrators 101A–101D and any one of the receiving piezoelectric vibrators 102A–102D.

Figure 3A:
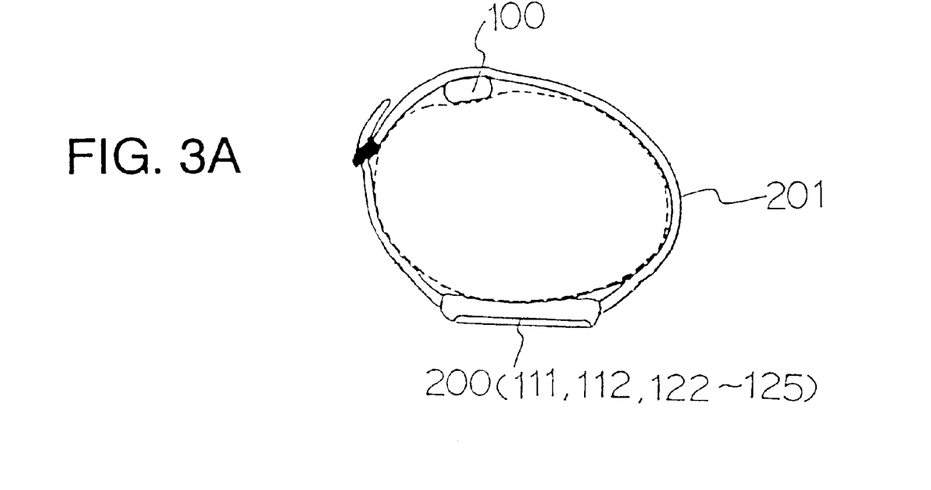
FIGS. 3A to 3C are view showing a state where the pulse wave detecting device is assembled in a timepiece.
Figure 3B:
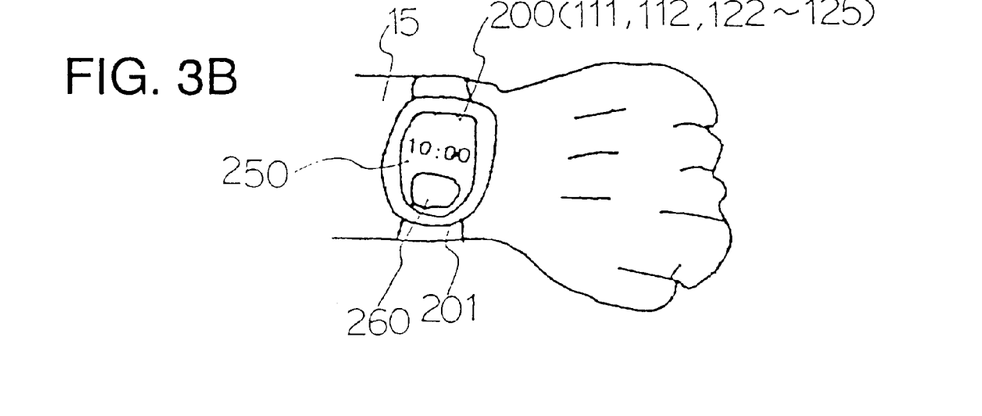
Figure 3C:
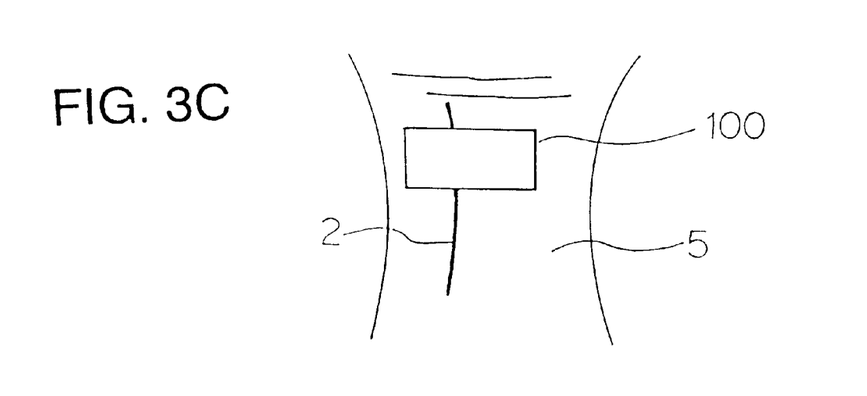

First, the user puts the pulse wave probe 100 on a body surface 5 such that the row of transmitting piezoelectric vibrators 101A–101D (or receiving piezoelectric vibrator 102A–102D) is nearly perpendicular to a radial artery 2 (see FIG. 3C).

Next, the user turns on a power to the pulse wave detecting device 1000. When turning on a power, the signal intensity measuring part 123 supplies a switch instruction signal for switching to any one of the transmitting piezoelectric vibrators 101A–101D to the switching part 111 via the signal line a. The driving part 112 drives any one of the transmitting piezoelectric vibrators 101A–101D switched by the switching part 111 so that an ultrasonic wave at a frequency of 32 KHz can be transmitted toward an artery 2.

The signal intensity measuring part 123 supplies a switch instruction signal for switching to any one of the transmitting piezoelectric vibrators 101A–101D to the switching part 111, and then a select instruction signal for selecting one per time of the receiving piezoelectric vibrators 102A–102D to the selecting part 121 via the signal line b.

In this manner, the signal intensity measuring part 123 controls to make totally 16 combinations each of any one of the transmitting piezoelectric vibrators 101A–101D and any one of the receiving piezoelectric vibrators 102A–102D, so that scan measurement on signal intensity can be made with using all these pairs.

After the receiving part 122 sequentially waveform-detects ultrasonic wave signals respectively supplied through the 16 pairs, the signal intensity measuring part 123 measures intensities of these signals and temporarily stores them to a not-shown memory part.

Next, the signal intensity measuring part 123 determines an optimal pair from among the totally 16 pairs of the transmitting piezoelectric vibrators 101A–101D and the receiving piezoelectric vibrators 102A–102D, based on the signal intensity data in temporary storage.

In this case, the signal intensity measuring part 123 determines as an optimal pair a maximum pair in value from the temporarily stored signal intensities.

Thus, an optimal pair is determined for pulse wave detection by the above operation, ending scan measurement.

Incidentally, a desired signal intensity value may be stored in the memory part of the signal intensity measuring part 123 so that an optimal pair can be taken by a closest pair in value to that signal intensity. This can prevent against unnecessary waste of power due to excessive signal intensity for pulse wave detection measurement.

Meanwhile, scan measurement may be made at a constant time interval except for a time after turning on a power to the pulse wave detecting device 1000. Also, where a signal intensity of an optimal pair weakens, scan measurement may be made again to predetermine an optimal pair thereby resuming a measurement.

By thus carrying out scan measurement, it is possible to monitor for enabling optimal pulse wave measurement with an optimal pair at all times.

(ii) Pulse wave detection measurement

Pulse wave measurement as explained below is made by an optimal pair of any one of the transmitting piezoelectric vibrators 101A–101D and any one of the receiving piezoelectric vibrators 102A–102D determined by the above-mentioned scan measurement.

First, the signal intensity measuring part 123 supplies a switch instruction signal to the switching part 111 through the signal line a to perform pulse wave detection with the optimal pair as determined in the scan measurement. This provides switching to a transmitting piezoelectric vibrator for the optimal pair (hereinafter referred to as "optimal transmitting piezoelectric vibrator") of the transmitting piezoelectric vibrators 101A–101D. A selection instruction signal is supplied to the selecting part 121 through the signal line b to select a receiving piezoelectric vibrator for the optimal pair (hereinafter referred to as "optimal receiving piezoelectric vibrator") of the receiving piezoelectric vibrators 102A–102D.

Now the below operation will be described on an assumption that in scan measurement (i) a transmitting piezoelectric vibrator 101B be determined as an optimal transmitting piezoelectric vibrator and a receiving piezoelectric vibrator 102C as a optimal receiving vibrator.

When starting a pulse wave detection measurement, an ultrasonic wave transmitted from the transmitting piezoelectric vibrator 101B and propagated through a human body including an artery 2 is received by the receiving piezoelectric vibrator 102C and supplied bypassing the selecting part 121 to the receiving part 122.

Next, the receiving part 122 waveform-detects the ultrasonic wave received by the receiving piezoelectric vibrator 102C.

The waveform-detected ultrasonic wave by the receiving part 122 is supplied to the signal processing part 124. Based on this signal, the signal processing part 124 counts a pulse frequency to form a pulse wave signal.

The pulse frequency and pulse wave signal counted by the signal processing part 124 are supplied to the output part 125. The output part 125 displays on the display part the pulse frequency and pulse wave signal supplied from the pulsation count part of the signal processing part 124.

Explanation will now be made on a state of detecting a pulse wave by a pulse wave detecting device 1000 built in a timepiece 200, with reference to FIG. 3A to FIG. 3C.

The pulse wave detecting device (timepiece) 1000 includes, as shown in FIG. 3A, a timepiece main body 200 and a strap 201. A pulse wave probe 100 is mounted as a pulse wave sensor on an inner surface of the strap 201.

As shown in FIGS. 3B and 3C, the timepiece 200 is put on a left (or right) wrist 5 with the timepiece main body 200 positioned on a back of the hand similarly to ordinary timepieces. In such a case, the pulse wave probe 100 can be adjusted in position so as to be over a radial artery by moving the pulse wave probe 100 in a lengthwise direction of the strap 201. The pulse wave probe 100 in its concrete arrangement form was described before and explanation thereof is omitted herein.

The timepiece main body 200 is arranged with a switching part 111, a driving part 112, a selecting part 121, a receiving part 122 a signal intensity measuring part 123, a signal processing part 124 and an output part 125, besides driving part such as a timepiece movement.

The driving part 112 may be used also as a driving circuit used in timepiece function.

Incidentally, the pulsation sensor 1000 and the timepiece main body 200 are connected by not-shown wiring built in the strap 201.

The timepiece main body 200 has a display surface (dial) having a timepiece display part 250 to display a time (day, day of the week, etc.) as a timepiece, and a display part 260 having a not-shown pulse frequency display part to display a pulse frequency and a not-shown pulse wave display part.

The signal processing part 124 has a pulse wave measuring part which supplies a pulse signal to the display part 260 each time detecting a pulse waveform peak. In response to the pulse signal, the pulse wave display part flickers in green. Seeing a flicker on the pulse wave display part 260, a user can visually recognize his or her pulse wave.

Incidentally, the flicker color of the pulse wave display part 260 may be changed depending on a pulse frequency, e.g. a pulse frequency of 69 and lower is represented by yellow flicker, 70 to 90 by blue flicker, 91 to 110 by green flicker, 111 to 130 by orange flicker, and 131 and higher by red flicker. The flickering color on the pulse wave display part 260, if changed in this manner, facilitates to distinguish a current pulse wave state.

(3) Modifications

The invention is not limited to the embodiments, and can adopt various modifications within the scope thereof as given below.

Note that in the below modifications explanations are centered on the modifications with the same constituent parts as those explained in the embodiments omitted to explain.

(a) First Modification

In the preferred embodiments as shown in FIG. 2A and FIG. 3C, where the pulse wave probe 100 is rested over a radial artery, the transmitting piezoelectric vibrators 101A–101D and the receiving piezoelectric vibrators 102A–102D were formed on the pulse wave substrate 150 such that any of the transmitting piezoelectric vibrators 101A–101D is positioned downstream (or upstream) the artery blood flow and any of the receiving piezoelectric vibrators 102A–102D upstream (or downstream) an artery 2.

Figure 4A:
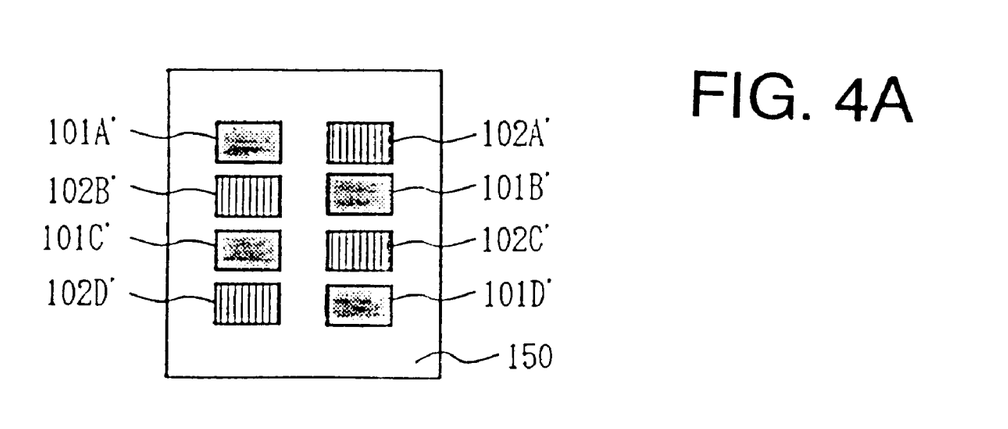
FIGS. 4A to 4C are view for explaining modifications in arrangement of piezoelectric vibrators on a pulse wave probe provided in the pulse wave detecting device.

On the contrary, in this first modification, as shown in FIG. 4A transmitting piezoelectric vibrators 101A'–101D' and receiving piezoelectric vibrators 102A'–102D' are formed on a pulse wave substrate 150 such that they are to be alternately positioned checkerwise at the upstream and downstream of the artery blood flow.

According to the first modification, proper pulse wave detection is possible even where for example there is no artery in an line form along a radius.

(b) Second Modification

In the preferred embodiment, as shown in FIG. 2B the four transmitting piezoelectric vibrators 101A–101D of the transmitting transducer 101 and the four receiving piezoelectric vibrators 102A–102D of the receiving transducer 102 are fitted in depressions formed from a top surface toward a backside of the pulse wave probe substrate 150 so that the piezoelectric vibrators are fixed substantially flush at their top surfaces with each other.

Figure 4B:
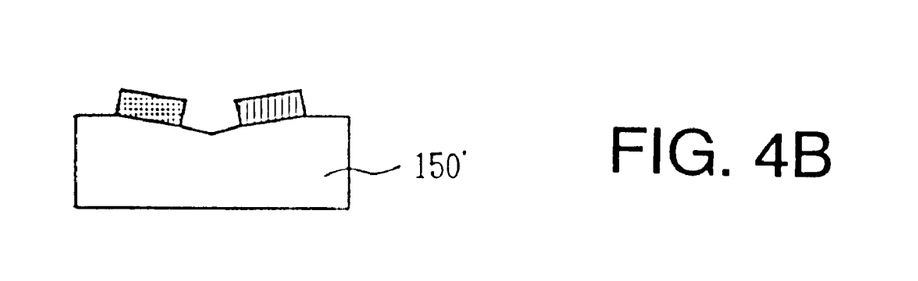
Figure 4C:
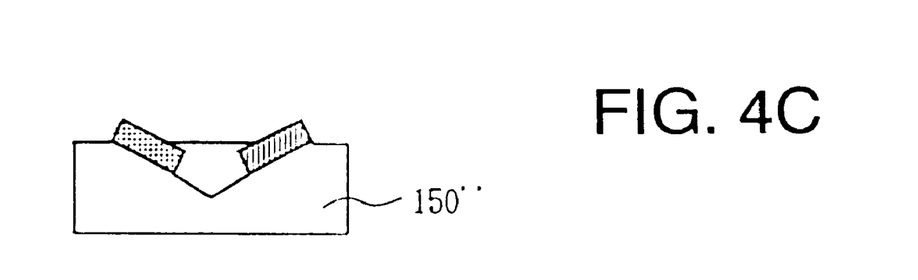

On the contrary, in this second modification, as shown in FIG. 4B and FIG. 4C a V-formed groove is formed lengthwise in the substrate from one edge portion to the other edge portion on the top surface thereof so that the piezoelectric vibrators are fixed slant on slopes of the groove.

According to the second modification, the receiving piezoelectric vibrators are easy to receive a ultrasonic wave transmitted from the transmitting piezoelectric vibrator and reflected back by the blood flowing through an artery.

(c) Third Modification

The sectional structure of the pulse wave probe of the first modification may adopt a structure of FIG. 4B or FIG. 4C of the second modification, besides the structure of FIG. 2B of the preferred embodiment.

Similarly, the sectional structure of the pulse wave probe 100 in FIG. 2A of the preferred embodiment may adopt a structure of FIG. 4B or FIG. 4C of the second modification, besides the structure of FIG. 2B of the preferred embodiment.

(d) Fourth Embodiment

In the above examples, explanations were made on the embodiments of the pulse wave count part that transmits a ultrasonic wave at 32-kHz frequency toward an artery to detect a pulsation from a ultrasonic wave signal attenuated and amplitude-modulated by a blood flow.

However, the piezoelectric vibrators 101A–101D of the transmitting transducer 101 is not limited in transmitting frequency to 32 kHz but can transmit a ultrasonic wave at an arbitrary frequency, i.e. selectable in a range of 20 kHz to 50 kHz, preferably 30 kHz to 40 kHz. Meanwhile, where the timepiece adopts another transmitting frequency m it is possible to use the same frequency m.

Meanwhile, pulsation detection may be made from an ultrasonic wave signal that is modulated in frequency by the Doppler effect caused due to a velocity of blood flow through an artery in place of using the pulse wave count part for detecting pulsation from an ultrasonic wave signal modulated of amplitude by artery blood flow. In such a case, an ultrasonic wave is transmitted at a higher frequency of about 10 MHz in order to cause the transmitted ultrasonic wave to be reflected upon the blood flowing through an artery. Thus, a pulse wave count part can be available that detects pulsation from a Doppler shift amount (frequency shift amount) in a received ultrasonic wave.

According to the present invention, the pulse wave probe can be automatically positioned in an optimal position when wearing the pulse wave detecting device.

Also, according to the invention, even if the pulse wave probe is deviated in position after wearing the pulse wave detecting device, the pulse wave probe can be newly, automatically positioned to an optimal position.

What is claimed is:

1. A pulse wave detecting device comprising:
   transmitting means having a plurality of transmitting piezoelectric vibrators to transmit an ultrasonic wave toward an artery;
   receiving means having a plurality of receiving piezoelectric vibrators to receive an ultrasonic wave propagated through the artery;
   pulse wave information acquiring means for acquiring pulse wave information from an ultrasonic wave signal transmitted from any one of the transmitting piezoelectric vibrators and received by any one of the receiving piezoelectric vibrators;
   signal intensity detecting means for detecting a signal intensity of the received ultrasonic wave by the receiving means; and
   optimal combination determining means for determining an optimal combination consisting of a single one of the transmitting piezoelectric vibrators to be used by the transmitting means to transmit the ultrasonic wave through the artery and a single one of the receiving piezoelectric vibrators to be used by the receiving means to receive the propagated ultrasonic wave based on the signal intensity of ultrasonic waves received by each of the respective receiving piezoelectric vibrators as detected by the signal intensity detecting means in response to the selection of various combinations of a transmitting piezoelectric vibrator and a receiving piezoelectric vibrator, and causing the transmitting piezoelectric vibrator of the optimal combination to transmit an ultrasonic wave and the receiving piezoelectric vibrator of the optimal combination to receive the ultrasonic wave for measurement by the pulse wave information acquiring means.

2. A pulse wave detecting device according to claim 1; wherein the optimal combination determining means has switching means for switching on any one of the transmitting piezoelectric vibrators so that the ultrasonic wave is transmitted from the one transmitting piezoelectric vibrator, and selecting means for selecting any one of the receiving piezoelectric vibrators so that the propagated ultrasonic wave is received by the one receiving piezoelectric vibrator, and means for causing the switching means and the selecting means to sequentially select different combinations of a respective one of the transmitting piezoelectric vibrators and a respective one of the receiving piezoelectric vibrators to determine the optimal combination of the transmitting piezoelectric vibrator and the receiving piezoelectric vibrator that produces at the signal intensity detecting means a maximum value in signal intensity of a received ultrasonic wave.

3. A pulse wave detecting device according to claim 2; wherein the optimal combination determining means causes the switching means and the selecting means to periodically sequentially select different combinations of a respective transmitting piezoelectric vibrator and a receiving piezoelectric vibrators to determine the optimal combination of the transmitting piezoelectric vibrator and the receiving piezoelectric vibrator that produces at the signal intensity detecting means a maximum value in signal intensity of a received ultrasonic wave.

4. A pulse wave detecting device according to claim 2; wherein the optimal combination determining means includes means for causing the switching means and the selecting means to sequentially select different combinations of a respective one of the transmitting piezoelectric vibrators and a respective one of the receiving piezoelectric vibrators to determine the optimal combination of the transmitting piezoelectric vibrator and the receiving piezoelectric vibrator that produces at the signal intensity detecting means a maximum value in signal intensity of a received ultrasonic wave when an ultrasonic wave detected by the signal intensity detecting means decreases in signal intensity.

5. A pulse wave detecting device according to claim 1; further comprising a substrate on which the transmitting piezoelectric vibrators and the receiving piezoelectric vibrators are mounted.

6. A pulse wave detecting device according to claim 5; wherein the transmitting piezoelectric vibrators are arranged in a row extending at an angle with respect to the artery when the pulse wave detecting device is mounted to a user's body.

7. A pulse wave detecting device according to claim 6; wherein the angle is about 90°.

8. A pulse wave detecting device according to claim 5; wherein the receiving piezoelectric vibrators are arranged in a row extending at an angle with respect to the artery when the pulse wave detecting device is mounted to a user's body.

9. A pulse wave detecting device according to claim 8; wherein the angle is about 90°.

10. A pulse wave detecting device according to claim 1; further comprising a substrate on which the transmitting piezoelectric vibrators and the receiving piezoelectric vibrators are mounted; wherein the transmitting piezoelectric vibrators are arranged in a first row and the receiving piezoelectric vibrators are arranged in a second row, and the first and second rows are adjacent to each other and extend at an angle with respect to the artery when the pulse wave detecting device is mounted to a user's body.

11. A pulse wave detecting device according to claim 10; wherein the angle is about 90°.

12. A pulse wave detecting device according to claim 1; wherein the pulse wave information acquiring means comprises a pulse frequency counter for counting a pulse frequency based on a signal supplied from the receiving means by measuring a time interval between pulse waves for a predetermined number of times and determining a pulse frequency per unit time interval based on a mean number of measurements.

13. A pulse wave detecting device according to claim 12; further comprising a display for displaying an output of the pulse wave information acquiring means.

14. A combination wristwatch and pulse monitor having a case, a strap for attaching the case to a user's wrist, a time counting device contained in the housing and having a clock signal generating circuit for generating a clock signal, and a pulse detecting device for detecting the user's pulse; wherein the pulse detecting device comprises the pulse wave detecting device according to claim 1, and the transmitting means drives the plurality of piezoelectric vibrators using the clock signal output by the clock signal generating circuit.

15. A combination wristwatch and pulse monitor according to claim 14; wherein the transmitting means and the receiving means are mounted to the strap so that the transmitting piezoelectric vibrators and the receiving piezoelectric vibrators are disposed against the user's wrist when the wristwatch is worn by the user.

16. A combination wristwatch and pulse monitor according to claim 15; wherein the transmitting piezoelectric vibrators and the receiving piezoelectric vibrators are mounted to the strap so that top surfaces of the vibrators are flush.

17. A combination wristwatch and pulse monitor according to claim 16; wherein the transmitting piezoelectric vibrators are arranged in a first row and the receiving piezoelectric vibrators are arranged in a second row, and the first and second rows are adjacent to each other and extend at an angle with respect to the artery when the wristwatch is worn by the user.

18. A combination wristwatch and pulse monitor according to claim 17; wherein the angle is about 90°.

* * * * *